US006921543B2

(12) United States Patent
Rudenko et al.

(10) Patent No.: US 6,921,543 B2
(45) Date of Patent: Jul. 26, 2005

(54) IMMUNOMODULATORY PREPARATION

(75) Inventors: Larisa G Rudenko, St Petersburg (RU); Robert Borland, Armadale (AU); Anatoly Naychin, St Petesburg (RU)

(73) Assignee: Pharmalink International Limited, Hong Kong (CN)

( * ) Notice: Subject to any disclaimer, the term of this patent is extended or adjusted under 35 U.S.C. 154(b) by 0 days.

(21) Appl. No.: 10/380,752

(22) PCT Filed: Sep. 21, 2001

(86) PCT No.: PCT/AU01/01180
§ 371 (c)(1),
(2), (4) Date: Jun. 19, 2003

(87) PCT Pub. No.: WO02/24211
PCT Pub. Date: Mar. 28, 2002

(65) Prior Publication Data
US 2004/0022810 A1 Feb. 5, 2004

(30) Foreign Application Priority Data
Sep. 22, 2000 (AU) .............................. PR0308

(51) Int. Cl.[7] .................. A61K 39/00; A61K 39/38; A61K 39/21; A61K 35/56; A61K 35/12
(52) U.S. Cl. .................... 424/547; 424/184.1; 424/450; 424/208.1; 424/776; 424/520; 424/522
(58) Field of Search .............. 424/184.1, 547, 424/520, 522, 206.1, 776; 435/69.1, 69.7; 530/327; 536/23.1; 623/23.75

(56) References Cited

U.S. PATENT DOCUMENTS

| 6,083,536 A | * | 7/2000 | Macrides et al. ........... 424/547 |
| 6,346,278 B1 | * | 2/2002 | Macrides et al. ........... 424/547 |
| 6,352,728 B1 | * | 3/2002 | Butters et al. .............. 424/776 |
| 6,759,057 B1 | * | 7/2004 | Weiner et al. .............. 424/450 |
| 2004/0022810 A1 | * | 2/2004 | Rudenko et al. ......... 424/208.1 |
| 2004/0228926 A1 | * | 11/2004 | Kendall et al. ............. 424/547 |

FOREIGN PATENT DOCUMENTS

| EP | 0468441 A | 1/1992 | |
| EP | 0615752 A | 9/1994 | |
| WO | WO 96/05164 | 2/1996 | |
| WO | WO 97/09992 | 3/1997 | |
| WO | WO 00/47225 | * 8/2000 | .......... A61K/39/00 |
| WO | WO 00/53198 | 9/2000 | |

OTHER PUBLICATIONS

Walte, JBC, 1983, 258/5:2911–2915.*
Shiels et al, Allergie et Immunologie, 2000, 32/7:279–282.*
Meletis, Alternative and Complementary Therapies, 2000, 6/3:141–144.*
Emelyanov et al, Eur. Respir. J., 2002, 20:596–600.*
Gibson et al, Comp. Ther. Med., 1998, 6:122–126.*
Whitehouse et al, Inflammopharmacology, 1997, 5:237–246.*
Harbison et al, Medical Journal of Australia, Nov. 2000, 173:560.*
Schroeder U et al., Nasal and parenteral Immunizations with diphtheria toxoid using monoglyceride/fatty acid lipid suspensions as adjuvants, *Vaccine*, 1999, 17(15–11): 2096–2103.
Friedman A et al., "Effect of dietary fatty acids on humoral immune response of turkeys, " British Poultry Science, 1997, 38(4): 342–248.
Sinclair A–J et al., "Marine lipids: overview 'News insights and llpid composition of LYPRINOL™,'" *Allergie et Immunologie*, 2000, 32(7):261–271.
Halpern GM, "Anti–inflammatory effects of a stabilized lipid extract of Perna canaliculus (Lyprinol)," *Allerg Immunol (Paris)*, 2000, 32: 272–278.

\* cited by examiner

*Primary Examiner*—N. M. Minnifield
(74) *Attorney, Agent, or Firm*—Pillsbury Winthrop Shaw Pittman LLP

(57) ABSTRACT

A method for modulating the immune response to an immunogen in a human or animal patient comprises administration to the patient of an immunogenically effective amount of the immunogen and an immunomodulatory effective amount of a lipid extract of *Perna canaliculus* or *Mytilus edulis*.

18 Claims, No Drawings

IMMUNOMODULATORY PREPARATION

This is the national phase of PCT International Application No. PCT/AU01/01180, filed Sep. 21, 2001, which is herein incorporated by reference in its entirety, and which claims priority to Australian Application No. PR 0308, filed Sep. 22, 2000.

FIELD OF THE INVENTION

This invention relates to a preparation having activity as an immunomodulatory substance, the preparation being a lipid extract of mussels, including the New Zealand green-lipped mussel, *Perna canaliculus*, and the blue mussel, *Mytilus edulis*. In particular, the invention relates to use of this lipid extract as an immunomodulatory agent or adjuvant, together with one or more immunogens, in an immunogenic preparation. Such an immunogenic preparation may be used as a vaccine, for example for prophylactic or therapeutic immunisation in treatment of bacterial, viral, fungal or protozoal infections in humans or non-human animals.

BACKGROUND OF THE INVENTION

The use of an adjuvant as a substance which results in a specific increase in the immunogenicity of an immunogen in a vaccine formulation is now well established. As outlined by Cox and Coulter (1992), "Advances in Adjuvant Technology and Application", in Animal Parasite Control Utilising Biotechnology, Chapter 4, Yong, W. K. CRC Press, adjuvants may possess activity in one or more of three broad categories, namely antigen presentation (the way in which individual antigen molecules are presented in a vaccine), antigen targeting (the efficacy with which the antigen payload is delivered to the appropriate effector cells of the immune system) and immune modulation (the mechanism which modifies the processing of antigens or epitopes by immune effector cells such that either the magnitude or the nature of the specific response is modified). A wide variety of adjuvants is now known. These include particulate adjuvants which are capable of forming microscopic aggregates where such aggregation is an important component of the adjuvant activity either as a result of improved presentation, improved targeting, or both. Such particulate adjuvants include aluminum salts, water-in-oil emulsions, oil-in-water emulsions, saponin (including Quil A and Iscoms), liposomes, proteosomes and microparticles (including microcapsules and microspheres). Other known adjuvants include non-particulate adjuvants which generally function by modulation of the immune response, although adjuvant presentation may be a component of their activity. These non-particulate adjuvants include peptides (such as muramyl dipeptide and its analogues), surface active molecules, nucleic acid derivatives, carbohydrate polymers, cytokines and lipid molecules. Adjuvant combinations are also well known, including Freund's complete adjuvant which combines the adjuvant activities of water-in-oil emulsions and microbacterial cells. In terms of the three discreet adjuvant functions: antigen presentation, antigen targeting, and immune modulation. the particulate adjuvants are efficient at antigen targeting, either by creating a depot to which macrophages are attracted or by being mobile and readily phagocytosed. Efficiency at antigen targeting does not effect the nature of the immune response, but will effect the economics of a vaccine by permitting a lower dose of antigen for a given effect. Immune modulation is the most complexed and least understood mode of adjuvant action. Some particulate adjuvants, particularly Iscoms, are highly immunomodulatory, however most of the others are non-immunomodulatory and require the addition of immunomodulatory molecules to enhance the immune response.

SUMMARY OF THE INVENTION

International Patent Application No. PCT/AU96/00564 discloses a preparation having anti-inflammatory activity, particularly anti-arthritic activity, which comprises a lipid extract of *Perna canaliculus* or *Mytilus edulis* rich in non-polar lipids, which is prepared by supercritical fluid extraction, for example, from crude mussel powder.

In work leading to the present invention, it has been demonstrated that the lipid extract disclosed in International Patent Application No. PCT/AU96/00564 is active as an immunomodulatory substance, stimulating the humoral, mucosal and cellular immune responses in a patient when administered with immunogen(s), such as influenza vaccine.

Accordingly, in one aspect the present invention provides a method for modulating the immune response to an immunogen in a human or animal patient, which comprises administration to the patient of an immunogenically effective amount of the immunogen and an immunomodulatory effective amount of a lipid extract of *Perna canaliculus* or *Mytilus edulis*.

Preferably, the lipid extract and immunogen are administered simultaneously, either separately or together in a single composition at the same time. However, they may be administered at separate times provided that they exert a combined effect in modulating the immune response in the patient. In a particularly preferred aspect, the lipid extract and immunogen are initially administered simultaneously, and the lipid extract is then subsequently administered alone for a further period (for example, for a further 7 to 28 or more days) in order to obtain and maintain effective blood levels of the lipid extract.

In another aspect, the present invention provides an immunogenic preparation comprising an immunogen and a lipid extract of *Perna canaliculus* or *Mytilus edulis*, optionally together with one or more pharmaceutically acceptable carriers or diluents.

The lipid extract and immunogen may be combined in a single composition, or alternatively they may be provided or supplied separately for use in combination with each other as described above.

The present invention also extends to the use of a lipid extract of *Perna canaliculus* or *Mytilus edulis* in the manufacture of an immunogenic preparation for use in modulating the immune response to an immunogen in a human or animal patient.

Further, the present invention extends to an agent for use in modulating the immune response to an immunogen in a human or animal patient, wherein the agent is a lipid extract of *Perna canaliculus* or *Mytilus edulis*.

DETAILED DESCRIPTION OF THE INVENTION

In work leading to the present invention it has been demonstrated that the lipid extract broadly described above has activity as an immunomodulator when administered with an influenza vaccine, and in particular this lipid extract stimulates the humoral, mucosal and cellular response of the patient to the influenza vaccine. In particular, this work has established that the lipid extract was active as an immunomodulator in stimulating the IgG response in patients receiving the influenza vaccine together with the lipid extract, compared with patients receiving the influenza vaccine only together with a placebo. In addition, in quantitative Nitroblue Tetrazolium tests as measurement of phagocytic activity, it has been demonstrated that the use of a lipid extract as immunomodulator does not suppress this activity.

As used herein the terms "vaccine" and "vaccination" extend to both prophylactic and therapeutic immunisation in treatment or therapy of bacterial, viral, fungal or protozoal infections in humans or animals. Reference herein to "modulating" or "modulation" of the immune response to an immunogen is a reference to regulation, particularly up-regulation or enhancement, of the immune response, for example by stimulation of the humoral, mucosal and/or cellular immune response to the immunogen.

Preferably, the lipid extract which is used in accordance with the present invention is an extract prepared by supercritical fluid extraction (SFE) of freeze-dried powdered mussel using a cryogenic fluid (such as cryogenic fluid $CO_2$) as the extracting medium. This method is described in International Patent Application No. PCT/AU96/00564, the contents of which are incorporated therein by reference. In comparison to solvent extraction techniques, supercritical fluid extraction using cryogenic fluid $CO_2$ produces a lipid extract rich in non-polar lipids, particularly in free fatty acids. While the exact composition of the lipid extract has not yet been established, it is known to contain not only free fatty acids (including unsaturated fatty acids), but also triglycerides, cholesterol esters and carotenes.

The immunogen which is incorporated into an immunogenic preparation or vaccine composition in accordance with this invention may be any chemical entity which can induce an immune response in a human or other animal, including but not limited to a humoral, mucosal and/or cell-mediated immune response to bacteria, viruses or other microorganisms.

The specific immunogen can be a protein or peptide, a polysaccharide, a lipopolysaccharide or a lipopeptide; or it can be a combination of any of these. More particularly, the specific immunogen can include a live attenuated or killed whole cell or organism, a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product. Examples of such immunogens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, haemophilias influenza, chlamydia, varicella-zoster virus, rabies or human immunodeficiency virus.

The formulation of such immunogenic or vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and is described, by way of example, in *Remington's Pharmaceutical Sciences,* 18th Edition, Mack Publishing Company, Pennsylvania, USA. Except insofar as any conventional media or agent is incompatible with the active immunogen, use thereof in the immunogenic compositions of the present invention is contemplated. Supplementary active components can also be incorporated into the compositions.

It is especially advantageous to formulate compositions in dosage unit form for ease of administration and uniformity of dosage. Dosage unit form as used herein refers to physically discrete units suited as unitary dosages for the human or animal patient to be treated; each unit containing a predetermined quantity of active component calculated to produce the desired therapeutic effect in association with the required pharmaceutical carrier and/or diluent. The specifications for the novel dosage unit forms of the invention are dictated by and directly dependent on (a) the unique characteristics of the active component and the particular therapeutic effect to be achieved, and (b) the limitations inherent in the art of compounding such an active component for the particular treatment.

Generally, daily doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of the active component.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces an acceptable therapeutic effect without causing clinically unacceptable adverse effects. Such modes of administration include oral, rectal, vaginal, topical, nasal, transdermal or parenteral (e.g. subcutaneous, intramuscular and intravenous) routes.

Oral administration will be preferred for many conditions because of the convenience to the patient, however nasal or parenteral administration may be more desirable in certain treatment regimes.

Compositions comprising the lipid extract may conveniently be presented in unit dosage form and may be prepared by any of the methods well known in the art of pharmacy. Such methods include the step of bringing the active components into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions suitable for oral administration may be presented as discrete units such as capsules, cachets, tablets or lozenges, each containing a predetermined amount of the active component(s), in liposomes or as a suspension in an aqueous liquid or non-liquid such as a syrup, an elixir, or an emulsion.

Compositions suitable for parenteral administration conveniently comprise a sterile aqueous preparation of the active component(s) which is preferably isotonic with the blood of the recipient. This aqueous preparation may be formulated according to known methods using those suitable dispersing or wetting agents and suspending agents. A sterile injectable preparation may be formulated as a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component(s) of the invention in sustained release pellets or capsules. Many types of sustained release delivery systems are available. These include, but are not limited to: (a) erosional systems in which the active component is contained within a matrix; and (b) diffusional systems in which the active component permeates at a controlled rate through a polymer.

As previously mentioned, the individual patient may be a human or other animal, including a livestock animal (e.g. sheep, cow or horse), laboratory test animal (e.g. mouse, rat, rabbit or guinea pig), companion animal (e.g. dog or cat) or wild animal.

An "immunologically effective amount" of an immunogen means that amount necessary at least partly to attain the desired immune response, or to delay the onset of, inhibit the progression of, or halt altogether, the onset or progression of the particular condition being treated. This amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Similarly, an "immunomodulatory effective amount" of an immunomodulator means that amount necessary to provide at least a detectable modulatory effect in the immunogenicity of the immunogen, preferably a detectable specific increase or enhancement in the immunogenicity of the immunogen. Once again, this amount will vary depending on the various factors set out above, however, this amount will also fall in a relatively broad range that can be determined through routine trials.

Throughout this specification, unless the context requires otherwise, the word "comprise", or variations such as "comprises" or "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

Further features of the present invention are more fully described in the following Example(s). It is understood, however, that this detailed description is included solely for the purposes of exemplifying the present invention, and should not be understood in any way as a restriction on the broad description of the invention as set out above.

EXAMPLE 1
A Preparation of Lipld Extract
A.1 Raw Material

The green lipped mussel (*Perna canaliculus*) is harvested on the south coast of New Zealand at which time the total mussel is stabilised with tartaric acid. Freeze drying results in a dry powder of pulverised form.

A.2 Extraction of Lipids

The technique of supercritical fluid extraction (SFE) is utilised to extract the biologically active lipids from the crude mussel powder. Cryogenic fluid $CO_2$ is used as the extracting medium. The $CO_2$ is expanded to atmospheric pressure and the extract is presented as a concentrated oil. The powder yields 3–3.5% of oil.

A.3 Profile of the Crude Oil

The extractable oil is orange amber in colour and is a viscous liquid at ambient temperature. The extract is stored below 4° C. and is handled in a nitrogen atmosphere. The crude oil shows strong UV activity and is protected from light to minimise the polymerisation of double bond components.

B Pilot Scale Supercritical Fluid Extraction

Extraction of total lipids in freeze-dried mussel powder. *Perna canaliculus* was performed on a pilot scale SFE unit undertaken at the Food Research Institute (Department of Agriculture, Werribee, Vic., Australia).

B.1 Instrumentation

Extractions were performed on a pilot scale extraction unit consisting of five basic sub-units (Distillers MG Limited., England, UK). The five basic units comprise: Carbon dioxide supply, Solids extraction, Primary separation, Evaporation and Tailing units.

The carbon dioxide supply unit consists of two $CO_2$ cylinders connected in parallel and placed on a weighing scale for recharging when appropriate. The extraction unit can be supplied with liquid SC—$CO_2$ and SC—$CO_2$. For this work the SFE unit was operated using SC—$CO_2$. Solid material was placed in the leaching column and the primary separator facilitates separation of extracted material by reduction of pressure (which allows extract to settle), adsorption or liquid extraction. The fluid extract was passed into the evaporation unit to evaporate the $CO_2$ by the use of internal heating tubes. The vapour may contain volatiles and thus it is subsequently passed to the tailing column to be scrubbed by pure liquid $CO_2$. The tailing unit traps the gaseous $CO_2$ from the evaporator unit and returns the volatile components to the evaporator.

B.2 Pilot Plant Extraction Procedure

Mussel powder (300 g) was charged to the extraction unit (leaching column). SC—$CO_2$ was delivered at a flow rate of 3.0 kg/h for two hours per extraction. Extractor temperature was set at 40° C. and the extractor pressure at 310 bar (4,500 psi). The evaporator temperature was held constant at 40° C. The mussel lipid extracts were stored under nitrogen at −10° C. in amber glass sealed containers.

EXAMPLE 2

The objective of this study was to investigate the immunomodulating properties of the lipid extract of Example 1, with particular reference to the effect of intake of the lipid extract on the humoral, mucosal and cellular immune systems and their responses to specific and non-specific antigenic challenge.

1. Preparations (a) The lipid extract prepared by the method of Example 1, herein referred to as LYPRINOL®, is a material with potent anti-inflammatory activity which is prepared from a stabilized marine mussel extract and contains polyunsaturated fatty acids (a unique grouping of elcosatetraenoic acids). It has been demonstrated that this lipid extract has high potency in helping people with disabilities relating to joint stiffness and swelling. The lipid extract was provided in soft gel capsules containing 50 mg LYPRINOL®, 100 mg Olive Oil as carrier, and 0.225 mg Vitamin E as anti-oxidant.

The placebo used was provided as soft gel capsules containing 150 rag Olive Oil, with the same appearances as the LYPRINOL® capsules. LYPRINOL® or placebo were taken by each individual at the dose rate of 4 capsules per day (2 in the morning and 2 at night with meals.)

(b) Russian trivalent live influenza vaccine (LIV), containing WHO recommended virus strains for 1998–99 influenza season was provided by the Institute for Experimental Medicine, St. Petersburg, Russia. Infectious activity of each of the live vaccine virus strains was approximately 7.0 lg EID50/0.2 ml. Intranasal placebo vaccine (LIP) consisted of reconstituted lyophilised uninfected allantoic fluid from embryonated hen's eggs in a volume equal to that of the vaccine. A 0.5 ml dose of live vaccine (LIV) or live placebo (LIP) was administered intranasally by sprayer (0.25 ml into each nostril).

2. Study Population.

40 adult (18–60 age range) volunteer study participants were assigned, in equal numbers, by stratified random sampling to one of four groups and received combinations of the following preparations:

| GROUP | No. | TREATMENT |
| --- | --- | --- |
| Group I | 10 people | (i) 4 LYPRINOL ® capsules/day for 28 days + |
| | | (ii) Live Influenza Vaccine (LIV) at day 0 |
| Group II | 10 people | (i) 4 ® capsules/day for 28 days + |
| | | (ii) Placebo Vaccine (LIP) at day 0 |
| Group III | 10 people | (i) 4 Placebo capsules/day for 28 days + |
| | | (ii) Live Influenza Vaccine (LIV) at day 0 |
| Group IV | 10 people | (i) 4 Placebo capsules/day for 28 days + |
| | | (ii) Placebo Vaccine (LIP) at day 0 |

3. Clinical Studies (i) Individuals in the study were monitored for symptoms of disease throughout the study and up to 1 month after taking the last capsule.

(ii) Female participants were excluded from the study if they were pregnant or could become pregnant during the course of the study.

(iii) All participants must have had no history of egg allergy or severe reactions to previous influenza vaccinations.

(iv) Participants should have had no acute illness and must have been afebrile (axillary temperature <37° C.) at the beginning of the study.

(v) The staff of the Institute of Experimental Medicine, St. Petersburg, coordinated recruitment and enrolment of volunteers for this study. They registered these individuals, collected blood specimens, administered vaccine or placebo.

4. Laboratory Studies

Specimen Collection

Ten ml of venous blood and nasal swab samples were collected from each volunteer at 3 time points:

(i) 0 time (prior to commencement study)
(ii) 28 days (at end of trial)
(iii) 56 days (28 days after taking last capsule) or 84 days (56 days after taking last capsules).

Each heparinized blood sample was separated into:
(i) Leukocytes fraction (white blood cells) peripheral blood lymphocytes (PBL) were isolated by Ficoll density gradient centrifugation
(ii) Plasma fraction Serum and nasal swab specimens were stored at −20° C.

Laboratory

The following parameters were measured from each blood or nasal swab sample:

Total serum immunoglobulins (IgG/IgM/IgA) were measured for B cell competence.

Systemic antibody in serum was analysed using the standard hemagglutination-inhibition (HI) test, including treatment of serum specimens with receptor-destroying enzymes. The type A(H1N1), type A(H3N2) and type B virus antigens used in the vaccines were used in all antibody detection assays.

Mucosal IgA antibody titres in nasal washes were evaluated using ELISA.

Lymphocyte function was measured using antigen- and mitogen-(phytohemagglutinin) conditioned blast-transformation.

Purified UV-inactivated influenza viruses were used to stimulate PBL.

Phytohemagglutinin (PHA) was used as a non-specific mitogen to test total T-cell responsiveness, and negative control cultures were used to assess the response of T-cells in culture medium alone.

The level of influenza virus-specific proliferation of PBL was determined using a standard 7 day proliferation assay incorporating $^3$H-thymidine into cultures of PBL stimulated with antigens described above.

Total and Differential White Blood cell Count.

Phagocytic Index of Polymorphonuclear Neutrophils (Microbicidal Activity).

4. Data Management, Participant Confidentiality and Informed Consent.

Each study participant was assigned a unique identification number (ID#). To ensure confidentiality, all written information and nasal swab and serum samples were identified by ID# only. Verbal informed consent was obtained from study participants by staff of the Institute of Experimental Medicine.

5. Results

The results of the study are set out in Tables 1 to 8.

Table 1: LYPRINOL® did not alter any of the white blood cell counts—all counts were within the normal range, i.e., there was no depression of the cellular elements following LYPRINOL®.

Table 2: LYPRINOL® treatment alone or in combination with a vaccine did not later the total immunoglobulin levels of serum, all levels were within the normal range.

Table 3: LYPRINOL®, in this study, markedly improved the percentage of volunteers giving a positive serum antibody response to a vaccination regime involving a tri-valent influenza vaccine.

Table 4: LYPRINOL® did not significantly after mucosal (secretory) antibody levels of vaccinated volunteers compared with vaccine alone.

Table 5: Using geometric mean titre assessment of activity (vaccine), this table shows that LYPRINOL®, in combination with vaccine gave a significant improvement in specific antibody response to the vaccine antigens when compared with vaccine alone. This table is a different mode of expressing results summarized in Table 3.

Table 6: The geometric mean table (compared with Table 4) shows that LYPRINOL® did not influence the mucosal antibody response of the vaccine.

Table 7: LYPRINOL® did not affect the phagocytosing ability of the body's polymorphonuclear neutrophil cells, which are largely responsible for clearing up and destroying invading microbes and small particles in the body. This ability to clean up (phagocytose) microbial agents is a key component of the body's defense mechanisms.

Table 8: LYPRINOL® did not depress the body's lymphocytic proliferative responses which are again another key component of the body's ability to protect itself from a variety of insults These results can be summarized as follows:
1. LYPRINOL® caused no suppression of systemic and local immune responses and no alteration in normal range values of the total and differential white cell count by the criteria investigated.
2. LYPRINOL® possessed rather powerful immunomodulating properties (likely with prolonged action) by enhancement of specific and partly local and cellular immunity stimulation.

TABLE 1

RESULTS OF TOTAL AND DIFFERENTIAL WHITE BLOOD CELLS COUNT.

| Group | No. of patients | No. of Sample | Leukocytes total/$\mu$l | Myelocytes | Neutrophiles (%) Meta-myelocytes | Neutrophiles (%) Stab neutrophiles | Neutrophiles (%) Mature forms of neutrophiles | Eosinophiles (%) | Basophiles (%) | Monocytes (%) | Lymphocytes (%) |
|---|---|---|---|---|---|---|---|---|---|---|---|
| Lyprinol | 10 | 1 | 4195 | 0 | 0 | 1.2 | 50.1 | 4.3 | 0.7 | 7.5 | 36.2 |
|  |  | 2 | 4230 | 0 | 0 | 3.5 | 40.8 | 4.0 | 0.7 | 4.5 | 46.5 |
|  |  | 3 | 5230 | 0 | 0 | 3.4 | 57.0 | 2.8 | 0.1 | 4.9 | 31.8 |
| Lyprinol + Vaccine | 10 | 1 | 5090 | 0 | 0.1 | 3.8 | 57.0 | 3.3 | 0.6 | 4.9 | 30.0 |
|  |  | 2 | 5335 | 0 | 0 | 2.7 | 44.7 | 3.0 | 1.0 | 4.0 | 44.6 |
|  |  | 3 | 6275 | 0 | 0 | 2.7 | 55.2 | 2.5 | 1.0 | 5.4 | 33.2 |
| Vaccine | 10 | 1 | 5960 | 0 | 0.1 | 2.2 | 60.2 | 3.5 | 0.5 | 5.5 | 28.0 |
|  |  | 2 | 5680 | 0 | 0 | 2.3 | 48.2 | 3.6 | 0.6 | 4.4 | 40.9 |
|  |  | 3 | 7075 | 0 | 0 | 2.1 | 56.2 | 3.5 | 0.4 | 4.2 | 32.8 |
| Placebo | 10 | 1 | 5394 | 0 | 0.1 | 3.0 | 54.2 | 2.8 | 0.9 | 7.7 | 31.5 |
|  |  | 2 | 5635 | 0 | 0.2 | 3.9 | 55.7 | 2.5 | 0.4 | 3.9 | 33.4 |
|  |  | 3 | 6110 | 0 | 0 | 3.6 | 62.3 | 1.6 | 0.4 | 4.7 | 27.0 |
| Standards eligible to Russia |  |  | 4000–9500 | 0 | 0 | 1–5% | 50–70% | 1–5% | 0.5–1.0% | 2–10% | 18–38% |

TABLE 2

TOTAL Ig CONCENTRATION IN SERUM.

| | | Arithmetic Mean Ig Concentration (mg/ml)** | | | | | | | | |
|---|---|---|---|---|---|---|---|---|---|---|
| | | IgG | | | IgA | | | IgM | | |
| Group | No. of Patients | 1* | 2* | 3* | 1 | 1 | 3 | 1 | 2 | 3 |
| Lyprinol | 10 | 11.2 | 10.3 | 10.5 | 1.9 | 1.8 | 1.7 | 1.1 | 1.1 | 1.2 |
| Lyprinol + Vaccine | 10 | 10.6 | 10.4 | 11.5 | 1.7 | 1.7 | 1.9 | 1.1 | 1.1 | 1.3 |
| Vaccine | 10 | 11.3 | 10.3 | 11.3 | 1.8 | 1.7 | 1.9 | 1.3 | 1.2 | 1.6 |
| Placebo | 10 | 11.7 | 11.7 | 11.2 | 1.9 | 1.9 | 1.9 | 1.1 | 1.1 | 1.3 |

*1-before study; 2 - 28 days after vaccination and first lyprinol taking; 3 - 56 days after last lyprinol taking,
**Russian standards:
IgG 8–16 mg/ml
IgA 1.4–4.2 mg/ml
IgM 0.5–1.9 mg/ml

TABLE 3

FREQUENCY OF SERUM ANTIBODY RESPONSES.

| | | Number (%) with 4-fold or greater rise HA antibodies to | | | | | |
|---|---|---|---|---|---|---|---|
| | | A/Perth/95/29 (H1N1) | | A/Sydney/97/76 (H3N2) | | B/Panama/4/E | |
| Group | No. of Patients | 1–2* | 1–3** | 1–2 | 1–3 | 1–2 | 1–3 |
| Lyprinol | 10 | 0 | 0 | 0 | 0 | 0 | 0 |
| Lyprinol + Vaccine | 10 | 6(60.0) | 6(60.0) | 3(30.0) | 6(60.0) | 5(50.0) | 6(60.0) |
| Vaccine | 10 | 3(30.0) | 3(30.0) | 3(30.0) | 4(40.0) | 2(20.0) | 3(30.0) |
| Placebo | 10 | 0 | 0 | 0 | 0 | 0 | 0 |

*conversions between first and second samples
**conversions between first and third samples.

TABLE 4

FREQUENCY OF SECRETORY IgA ANTIBODY RESPONSES.

| | | Number (%) with 4-fold or greater rise IgA ELISA antibodies to | | | | | |
|---|---|---|---|---|---|---|---|
| | | A/Beijing/262/95 (H1N1) | | A/South Africa/1147/76 (H3N2) | | B/Harbin/07/94 | |
| Group | No. of Patients | 1–2* | 1–3** | 1–2 | 1–3 | 1–2 | 1–3 |
| Lyprinol | 10 | 0 | 0 | 0 | 0 | 0 | 0 |
| Lyprinol + vaccine | 10 | 6(60.0) | 3(30.0) | 4(40.0) | 4(40.0) | 4(40.0) | 1(10.0) |
| Vaccine | 10 | 9(90.0) | 3(30.0) | 5(50.0) | 2(20.0) | 3(30.0) | 0 |
| Placebo | 10 | 0 | 0 | 0 | 0 | 0 | 0 |

*convervions between first and second samples,
**conversions between first and third samples.

TABLE 5

DYNAMIC OF GEOMETRIC MEAN TITERS OF SERUM ANTIBODIES.

| | | Geometric Mean Titers (GMT) | | | | | | | | | | | |
|---|---|---|---|---|---|---|---|---|---|---|---|---|---|
| | No. of | A/Perth/95/29 (H1N1) | | | | A/Sydney/97/76 (H3N2) | | | | B/Panama/4/E | | | |
| Group | Patients | 1* | 2* | 3* | 3/1** | 1 | 2 | 3 | 3/1 | 1 | 2 | 3 | 3/1 |
| Lyprinol | 10 | 17 4.1 ± 0.82" | 19 4.2 ± 0.85 | 20 4.3 ± 0.83 | 1.2 | 16 4.0 ± 0.88 | 17 4.1 ± 0.91 | 19 4.2 ± 0.90 | 1.1 | 19 4.2 ± 0.80 | 19 4.2 ± 0.80 | 24 4.6 ± 0.78 | 1.3 |
| Lyprinol + Vaccine | 10 | 16 4.0 ± 0.93 | 43 5.4 ± 1.03 | 43 5.4 ± 0.99 | 2.7 | 11 3.4 ± 0.74 | 23 4.5 ± 0.76 | 33 5.0 ± 0.78 | 3.0 | 11 3.4 ± 0.74 | 26 4.7 ± 0.89 | 35 5.1 ± 0.70 | 3.2 |
| Vaccine | 10 | 9 3.2 ± 0.62 | 18 4.1 ± 0.91 | 20 4.3 ± 0.92 | 2.2 | 8 3.0 ± 0.59 | 13 3.7 ± 0.78 | 16 4.0 ± 0.78 | 2.0 | 9 3.2 ± 0.62 | 14 3.8 ± 0.89 | 16 4.0 ± 0.83 | 1.8 |
| Placebo | 10 | 12 3.5 ± 0.64 | 12 3.5 ± 0.64 | 12 3.5 ± 0.64 | 1.0 | 9 3.2 ± 0.74 | 9 3.2 ± 0.74 | 9 3.2 ± 0.74 | 1.0 | 16 4.0 ± 0.93 | 14 3.8 ± 0.79 | 13 3.7 ± 0.78 | 0.8 |

*1-before study; 2–28 days after vaccination and first lyprinol taking; 3–56 days after last lyprinol taking.
**GMT RISE (GMT of third sample/GMT of first sample)
"LogGMT ± sem

TABLE 6

DYNAMIC OF GEOMETRIC MEAN TITERS OF SECRETORY IgA ANTIBODIES.

| | | Geometric Mean Titers (GMT) | | | | | | | | | | | |
|---|---|---|---|---|---|---|---|---|---|---|---|---|---|
| | No. of | A/Beijing/262/95 (H1N1) | | | | A/South Africa/1147/76 (H3N2) | | | | B/Harbin/07/94 | | | |
| Group | Patients | 1* | 2* | 3* | 2/1** | 1 | 2 | 3 | 2/1 | 1 | 2 | 3 | 2/1 |
| Lyprinol | 10 | 20 4.3 ± 0.42 | 21 4.4 ± 0.48 | 16 4.0 ± 0.61 | 1.1 | 28 4.8 ± 0.29 | 28 4.8 ± 0.29 | 28 4.8 ± 0.29 | 1.0 | 10 3.0 ± 0.82 | 11 3.4 ± 0.27 | 15 3.9 ± 0.35 | 1.1 |
| Lyprinol + Vaccine | 10 | 6 2.6 ± 0.22 | 16 4.0 ± 0.39 | 13 3.7 ± 0.33 | 2.7 | 11 3.5 ± 0.34 | 23 4.5 ± 0.58 | 26 4.7 ± 0.56 | 2.1 | 6 2.5 ± 0.22 | 11 3.5 ± 0.34 | 9 3.1 ± 0.35 | 1.8 |
| Vaccine | 10 | 11 3.5 ± 0.43 | 56 5.8 ± 0.55 | 28 4.8 ± 0.53 | 5.1 | 9 3.1 ± 0.28 | 20 4.3 ± 0.37 | 14 3.9 ± 0.35 | 2.2 | 8 2.9 ± 0.88 | 13 3.7 ± 0.33 | 10 3.3 ± 0.30 | 1.6 |
| Placebo | 10 | 17 4.1 ± 0.35 | 16 4.0 ± 0.33 | 16 3.0 ± 0.58 | 0.9 | 13 3.7 ± 0.21 | 12 3.6 ± 0.27 | 12 3.6 ± 0.34 | 0.9 | 8 3.0 ± 0.21 | 8 3.0 ± 0.21 | 8 3.0 ± 0.21 | 1.0 |

*1-before study; 2–28 days after vaccination and first lyprinol taking; 3–56 days after last lyprinol taking.
**GMT RISE (GMT of second sample/GMT of first sample)
"LogGMT ± sem

TABLE 7

RESULTS OF QUANTITATIVE NITROBLUE TETRAZOLIUM TEST.

| | | Optical Density (Arithmetic mean) | | | | | | | | |
|---|---|---|---|---|---|---|---|---|---|---|
| | No. of | Nonstimulated neutrophils | | | Stimulated neutrophils | | | Stimulation Index | | |
| Group | Patients | 1* | 2* | 3* | 1 | 2 | 3 | 1 | 2 | 3 |
| Lyprinol | 10 | 0.193 ± 0.04 | 0.145 ± 0.05 | 0.206 ± 0.04 | 0.322 ± 0.03 | 0.208 ± 0.05 | 0.242 ± 0.06 | 1.67 | 1.44 | 1.17 |
| Lyprinol + Vaccine | 10 | 0.245 ± 0.04 | 0.127 ± 0.05 | 0.202 ± 0.05 | 0.297 ± 0.04 | 0.191 ± 0.04 | 0.263 ± 0.07 | 1.21 | 1.50 | 1.30 |

TABLE 7-continued

RESULTS OF QUANTITATIVE NITROBLUE TETRAZOLIUM TEST.

| | | Optical Density (Arithmetic mean) | | | | | | | | |
|---|---|---|---|---|---|---|---|---|---|---|
| | No. of | Nonstimulated neutrophils | | | Stimulated neutrophils | | | Stimulation Index | | |
| Group | Patients | 1* | 2* | 3* | 1 | 2 | 3 | 1 | 2 | 3 |
| Vaccine | 10 | 0.251 ± 0.04 | 0.107 ± 0.04 | 0.182 ± 0.04 | 0.334 ± 0.05 | 0.153 ± 0.04 | 0.230 ± 0.05 | 1.33 | 1.43 | 1.26 |
| Placebo | 10 | 0.218 ± 0.05 | 0.137 ± 0.05 | 0.247 ± 0.05 | 0.328 ± 0.07 | 0.239 ± 0.07 | 0.328 ± 0.08 | 1.51 | 1.73 | 1.33 |

*1-before study; 2–28 clays after vaccination and first taking lyprinol: 3–56 days alter last iyprinol taking.

TABLE 8

PROLIFERATIVE IMMUNE RESPONSE OF LYMPHOCYTE CULTURES IN VITRO

| | | | 1* | | 2* | | 3* | |
|---|---|---|---|---|---|---|---|---|
| Group | No. of Patients | Antigen, Mitogen | Net CPM** | S.I.*** | Net CPM | S.I. | Net CPM | S.I. |
| Lyprinol | 10 | A(H1N1) | 227 | 1.17 | 379 | 1.24 | 558 | 1.56 |
| | | PHA | 13707 | 6.31 | 8506 | 5.78 | 6670 | 7.36 |
| Lyprinol + Vaccine | 10 | A(H1N1) | 498 | 1.51 | 5092 | 2.59 | 465 | 1.36 |
| | | PHA | 2386 | 2.51 | 12575 | 4.31 | 6434 | 5.12 |
| Vaccine | 10 | A(H1N1) | 339 | 1.09 | 101 | 1.03 | 318 | 1.24 |
| | | PHA | 2241 | 1.64 | 5085 | 2.80 | 7158 | 5.55 |
| Placebo | 10 | A(H1N1) | 440 | 1.19 | 555 | 1.46 | 141 | 1.13 |
| | | PHA | 8230 | 4.31 | 2456 | 2.52 | 2879 | 3.24 |

*1-before study; 2–28 days after vaccination and taking lyprinol; 3–56 days after last lyprinol taking.
**Net CPM = CPMstimulated − CPMspontaneous
***S.I.—stimulation index = CPMstimulated/CPMspontaneous

What is claimed is:

1. A method for modulating the immune response to an immunogen in a human or animal patient, wherein said method comprises administering to said patient an immunogenically effective amount of said immunogen and an immunomodulatory effective amount of a lipid extract of *Perna canaliculus*.

2. The method according to claim 1, wherein said immunogen and said lipid extract are administered simultaneously to said patient.

3. The method according to claim 1, wherein said immunogen and said lipid extract are administered separately to said patient.

4. The method according to claim 1, wherein said immunogen and said lipid extract are initially administered simultaneously to said patient, and subsequently said lipid extract is separately administered to said patient.

5. A method for modulating the immune response to an immunogen in a human or animal patient, wherein said method comprises administering to said patient an immunogenically effective amount of said immunogen and an immunomodulatory effective amount of a lipid extract of *Perna canaliculus*, whereby said immunogen elicits an immune response against viral or bacterial hepatitis, influenza, diphtheria, tetanus, pertussis, measles, mumps, rubella, polio, pneumococcus, herpes, respiratory syncytial virus, haemophilias influenza, chlamydia, varicella-zoster virus, rabies or human immunodeficiency virus.

6. The method according to claim 5, wherein said immunogen is an influenza immunogen.

7. The method according to claim 6, wherein said immunogen is live influenza vaccine.

8. The method according to claim 1, wherein said lipid extract is prepared by supercritical fluid extraction.

9. The method according to claim 8, wherein cryogenic fluid $CO_2$ is used in said supercritical fluid extraction.

10. The method for the manufacture of an immunogenic preparation for use in modulating the immune response to an immunogen in a human or animal patient, which comprises admixing an immunogenically effective amount of said immunogen and an immunomodulatory effective amount of a lipid extract of *Perna canaliculus*.

11. An immunogenic preparation comprising an immunogen and a lipid extract of *Perna canaliculus*, optionally together with one or more pharmaceutically acceptable carriers or diluents.

12. The preparation according to claim 11, wherein said immunogen and said lipid extract are formulated for simultaneous administration or for sequential administration in either order.

13. The preparation according to claim 11, wherein said immunogen and said lipid extract are formulated as a single composition.

14. An immunogenic preparation comprising an immunogen and a lipid extract of *Perna canaliculus*, optionally together with one or more pharmaceutically acceptable carriers or diluents, wherein said immunogen, upon administration to a human or animal patient, elicits an immune response against viral or bacterial hepatitis, influenza, diphtheria, tetanus, pertussis, measles, mumps, rubella, polio, pneumococcus, herpes, respiratory syncytial virus, haemophilias influenza, chlamydia, varicella-zoster virus, rabies or human immunodeficiency virus.

15. The preparation according to claim 14, wherein said immunogen is an influenza immunogen.

16. The preparation according to claim 15, wherein said immunogen is live influenza vaccine.

17. The preparation according to claim 11, wherein said lipid extract in prepared by supercritical fluid extraction.

18. The preparation according to claim 17, wherein cryogenic fluid $CO_2$ is used in said supercritical fluid extraction.

* * * * *